US 6,364,853 B1

(12) United States Patent
French et al.

(10) Patent No.: US 6,364,853 B1
(45) Date of Patent: Apr. 2, 2002

(54) IRRIGATION AND SUCTION VALVE AND METHOD THEREFOR

(75) Inventors: C. Kenneth French, Cranfills; Garrett L. Barker, Meridian, both of TX (US); Stephen Chakoff; Melvin E. Levinson, both of Miami, FL (US)

(73) Assignee: Scion International, Inc., Miami, FL (US)

( * ) Notice: Subject to any disclaimer, the term of this patent is extended or adjusted under 35 U.S.C. 154(b) by 0 days.

(21) Appl. No.: 09/659,739

(22) Filed: Sep. 11, 2000

(51) Int. Cl.[7] .................................................. A61M 1/00
(52) U.S. Cl. ..................... 604/35; 604/118; 604/250; 137/596.2; 251/9
(58) Field of Search ................ 604/537, 30, 33–35, 604/118, 902, 250, 249; 137/596.2; 251/9, 263, 322, 323

(56) References Cited

U.S. PATENT DOCUMENTS

| 3,046,802 | A |   | 7/1962  | Cupedo |
|-----------|---|---|---------|--------|
| 3,220,695 | A |   | 11/1965 | Downey et al. |
| 4,106,508 | A |   | 8/1978  | Berlin ........................ 128/346 |
| 4,221,236 | A |   | 9/1980  | Rosenberg ............. 137/624.11 |
| 4,221,238 | A |   | 9/1980  | Madsen ................... 137/627.5 |
| 4,383,477 | A |   | 5/1983  | Nilsson et al. ............ 98/41 AV |
| 4,680,026 | A | * | 7/1987  | Weightman et al. .......... 604/33 |
| 4,708,717 | A | * | 11/1987 | Deane et al. ................. 604/35 |
| 4,771,985 | A |   | 9/1988  | Gross et al. .................. 251/38 |
| 4,852,551 | A | * | 8/1989  | Opie et al. ..................... 128/4 |
| 4,883,472 | A |   | 11/1989 | Michel ........................ 604/208 |
| 4,956,755 | A |   | 9/1990  | Maglica et al. ............. 362/206 |
| 5,188,591 | A |   | 2/1993  | Dorsey, III ................... 604/33 |
| 5,195,959 | A | * | 3/1993  | Smith ........................... 604/34 |
| 5,228,646 | A | * | 7/1993  | Raines ......................... 251/95 |
| 5,279,549 | A | * | 1/1994  | Ranford ....................... 604/34 |
| 5,391,145 | A |   | 2/1995  | Dorsey, III ................... 604/33 |
| 5,421,552 | A |   | 6/1995  | Wang et al. ................. 251/230 |
| 5,447,494 | A |   | 9/1995  | Dorsey, III ................... 604/43 |
| 5,456,448 | A |   | 10/1995 | Chou .......................... 251/230 |
| 5,487,649 | A |   | 1/1996  | Dorsey, III et al. ......... 417/395 |

(List continued on next page.)

*Primary Examiner*—Angela D. Sykes
*Assistant Examiner*—Cris Rodriguez
(74) *Attorney, Agent, or Firm*—Robert C. Kain, Jr.; Fleit, Kain

(57) ABSTRACT

The in-line hand operated valve controls the flow of at least one, and preferably both, irrigation fluid and suction respectively to and from a surgical site via a delivery line. In one working embodiment, suction fluid is supplied to the valve via a first source line and suction is supplied to the valve via a second source line. The valve body defines, source ports in fluid communication with the source lines and a delivery port in fluid communication with the delivery line. The valve body includes at least one, and preferably two, collapsible internal fluid carrying channels in fluid communication with the respective source port and the delivery port. Each valve mechanism includes an operator control surface, a stem, and a compressor member acting on and closing and opening the collapsible segment of the fluid carrying channel or body. A biasing element (such as a spring or other resilient body) keeps the valve stem and the compressor element in either an open or a closed state. A two position interlocking mechanical switch is coupled to the valve stem. In one position, the compressor element is extended and is the ON valve position and in a second position, the compressor element is withdrawn to achieve the OFF valve position. Preferably, operator control surfaces are disposed on opposing side wall surfaces of the generally cylindrical or torpedo shaped valve body. When closed, and the operator control surfaces are substantially co-extensive with the cylindrical or torpedo shaped valve body. The method of providing a valve control utilizes these shape and click open and click close systems.

17 Claims, 7 Drawing Sheets

SURGICAL SITE 1

U.S. PATENT DOCUMENTS

| | | | |
|---|---|---|---|
| 5,522,796 A | 6/1996 | Dorsey, III | 604/118 |
| 5,546,983 A | 8/1996 | Clare | 137/607 |
| 5,573,504 A | 11/1996 | Dorsey, III | 604/35 |
| 5,586,977 A | 12/1996 | Dorsey, III | 604/264 |
| 5,588,634 A * | 12/1996 | Nettekoven | 251/9 |
| 5,599,314 A | 2/1997 | Neill | 604/207 |
| 5,674,204 A | 10/1997 | Chanoch | 604/211 |
| 5,679,111 A | 10/1997 | Hjertman et al. | 604/135 |
| 5,692,729 A * | 12/1997 | Harhen | 251/4 |
| 5,707,351 A | 1/1998 | Dorsey, III | 604/30 |
| 5,803,510 A | 9/1998 | Dorsey, III | 285/148.23 |
| 5,806,404 A | 9/1998 | Sher | 92/31 |
| 5,830,214 A * | 11/1998 | Flom et al. | 606/41 |

* cited by examiner

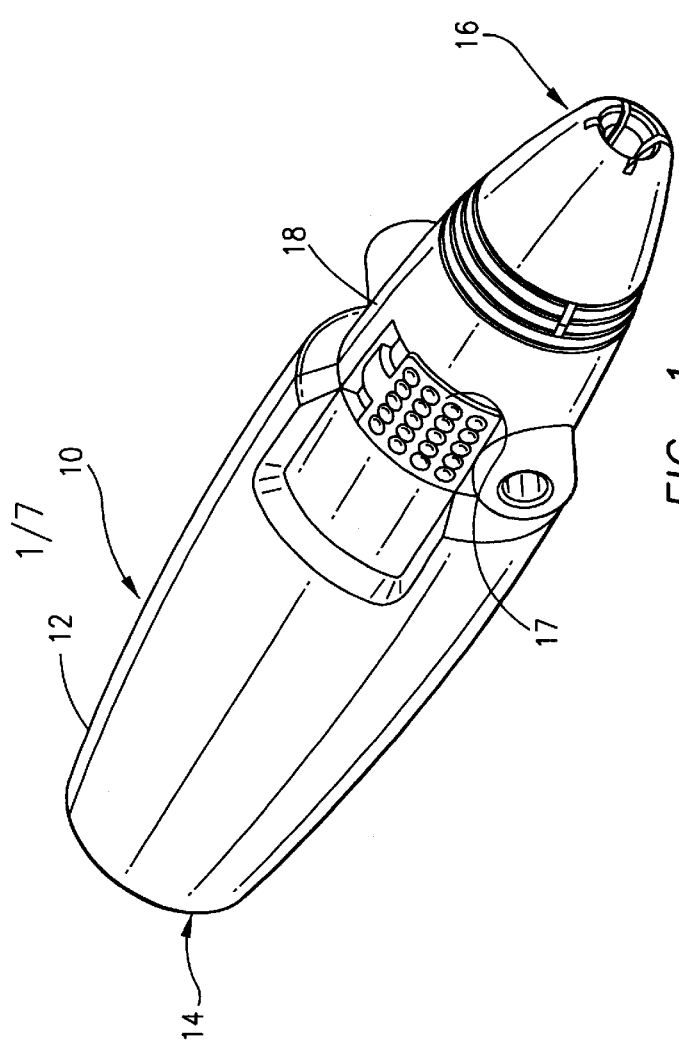
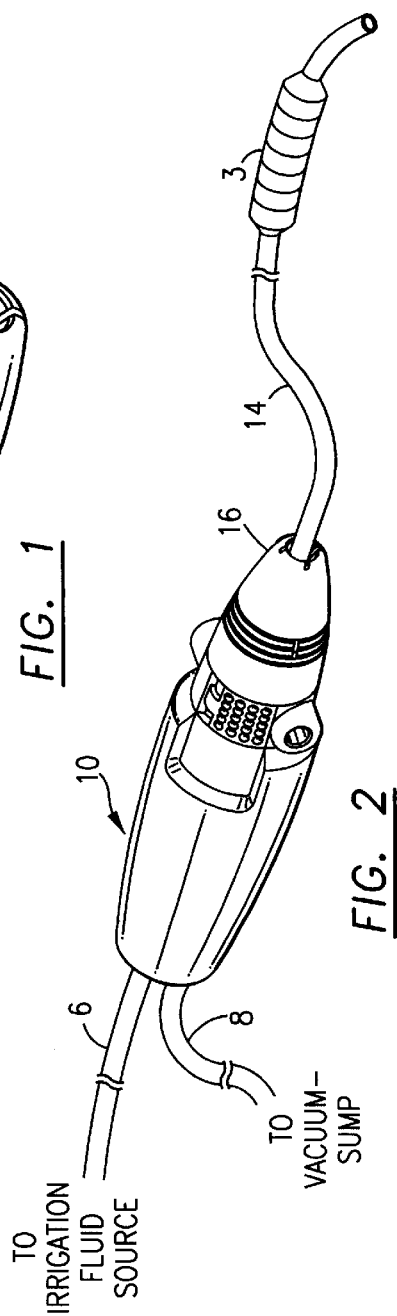
FIG. 1
FIG. 2

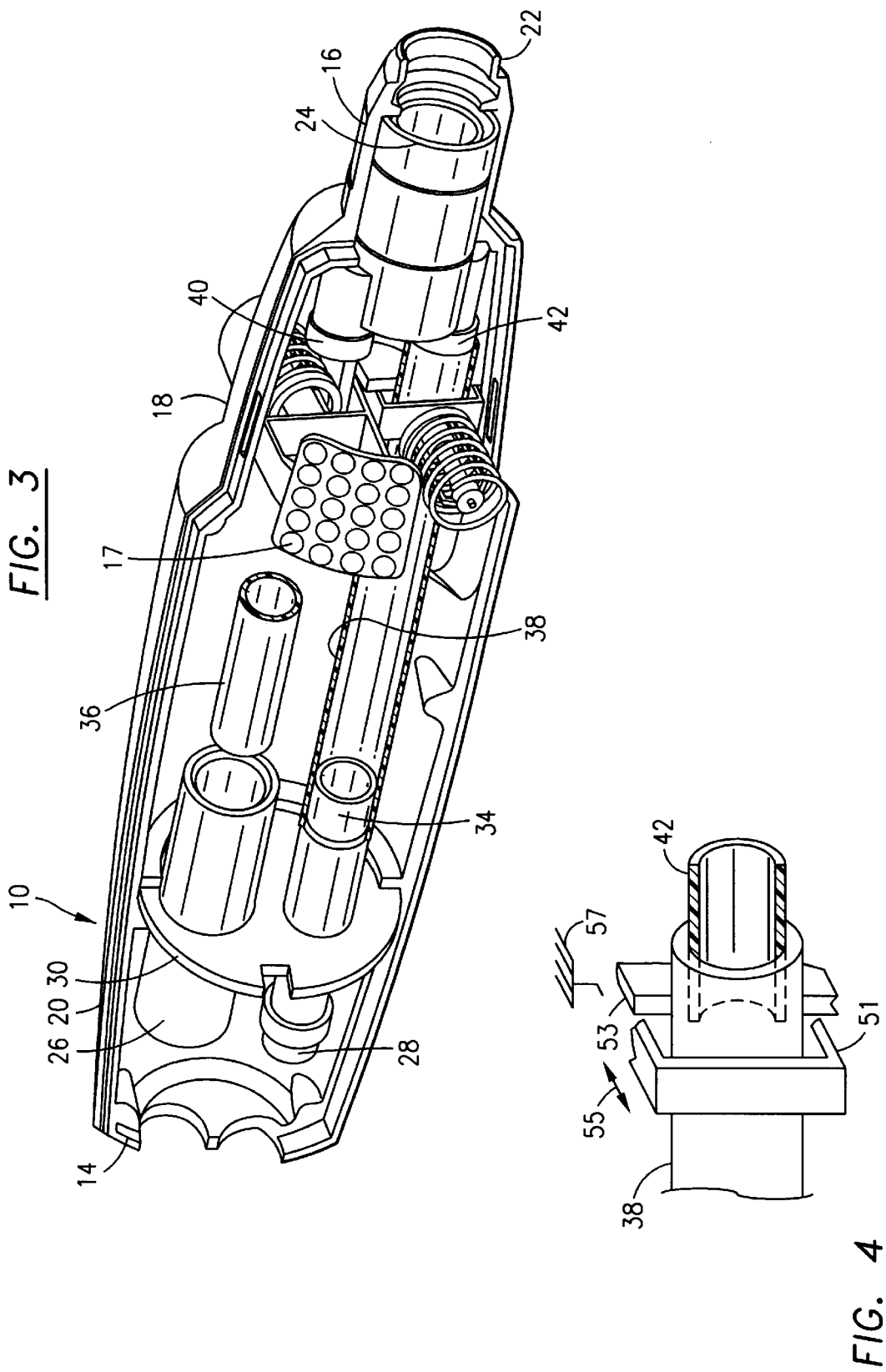

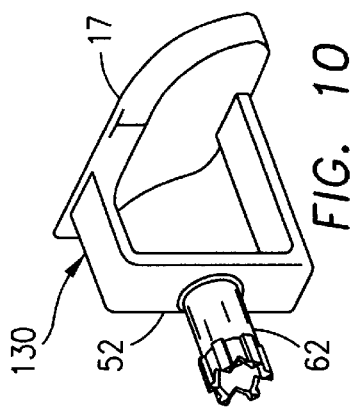
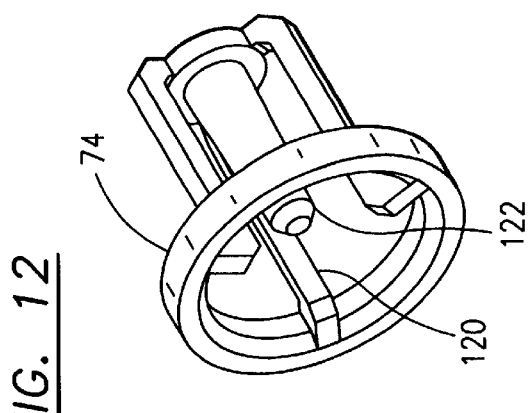
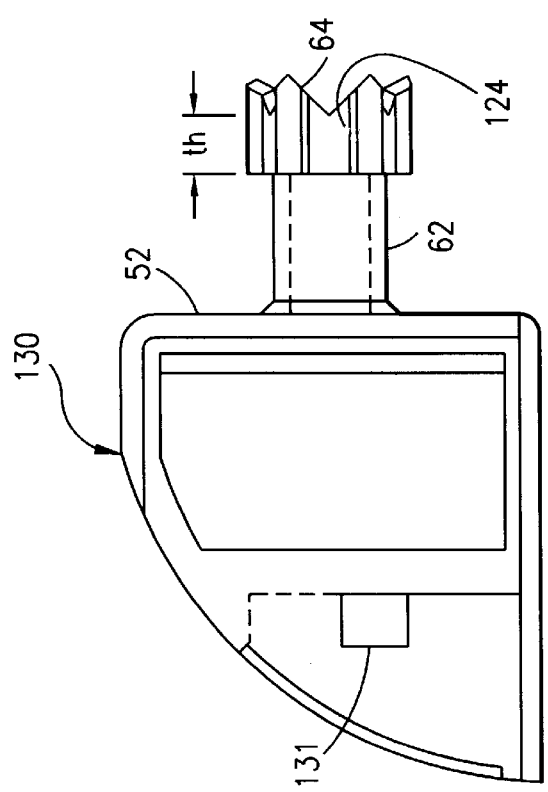
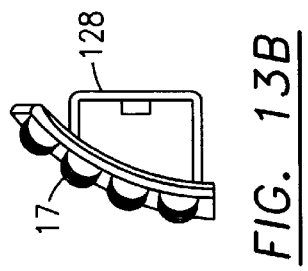
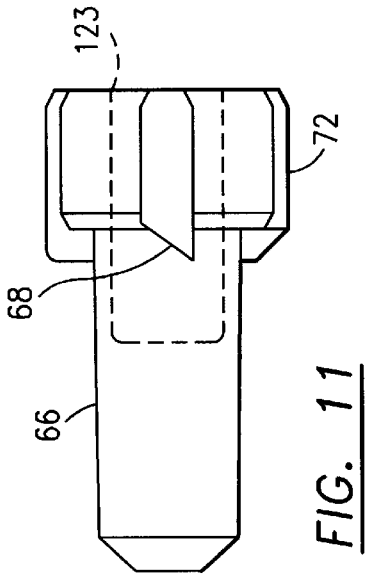

IRRIGATION AND SUCTION VALVE AND METHOD THEREFOR

The present invention relates to a hand operated valve for controlling the flow of at least one, and preferably both, irrigation fluid and suction to and from a surgical site and a valving method therefor.

During medical procedures, it is common to irrigate or wash a wound with sterilized fluid (herein "irrigation fluid"). Further, during laproscopic surgical procedures, the physician or other health professional (sometimes herein identified as "an operator") may utilize the irrigation fluid for hydrodissection. In both procedures, the irrigation fluid is provided via a source line from a source or reservoir of fluid. Many times, the irrigation fluid is provided under pressure (for example, 5–15 psi) to the surgical site.

Physicians and other health professionals also utilize suction to remove spent irrigation fluid, other bodily fluids and debris which may accumulate at the wound site or surgical site. In certain medical procedures, the physician utilizes suction to remove gas. Gas is sometimes used to create an operable cavity at a laproscopic surgical site. Suction, or negative air pressure (some pressure below the ambient pressure), is created in a suction source line via a vacuum source and a sump. As used herein, the term "suction source" or "source of suction" refers to a supply of negative air pressure. Although from a strictly scientific view point, suction is not created from "a suction source," the negative pressure developed by the vacuum pump is a resource used by the physician or other health professional. If the vacuum pump fails to operate properly, the resource or source of suction is no longer available to the physician. In a similar manner, if the reservoir of the irrigation fluid dissipates, the source of irrigation fluid is no longer available for use by the physician. In this sense, the present invention utilizes a source of suction.

U.S. Pat. No. 5,522,796 to Dorsey discloses a metered and gauged trumpet valve utilized to control irrigation fluid to a surgical site and suction applied to a suction line leading to the surgical site. As disclosed in Dorsey '796, the output of the metering valve is a single delivery line leading to the surgical site. Irrigation fluid is turned ON and OFF via the valve control and suction is turned ON and OFF based the controllable positions of valve stems in the metering valve. The Dorsey '796 metering valve includes a rotatable operator control surface which has a normally disposed plate with a slope control or a cam surface. A generally cylindrical valve stem has a shoulder about its periphery upon which rests a gear having sloped control shapes or a sloped cam surface. The gear is keyed to the cylindrical valve stem. When the operator rotates the operator control surface, the cam shaped valve control surface affixed to the operator control rotates thereby changing the contact point on the sloping cam surface. The control sloping cam surface moves on the sloped cam surface of the valve stem gear thereby changing the vertical limit or stop position of the valve stem. By rotating the operator control surface, the valve opens to one of several gauge positions. At the other end of the valve stem, flow control is achieved between the stem and a valve body. The valve stem is biased in a direction to either fully open or fully close the irrigation and/or suction flow through the valve body. Preferably, the valve is biased closed. The physician can provide variable flow control by depressing the valve stem against the biasing enforce of the spring thereby opening or closing the valving aperture and the valve body. By rotating the control surface, the physician can establish preset flow control points or limits for the throw of the valve stem. An example of the use of a preset flow control is providing a low level of irrigation fluid at the surgical site. At the same time, the physician may operate the suction control valve from a fully OFF position to a fully ON position by depressing the valve stem vertically thereby opening the valving aperture between the valve stem and the valve body. In a preferred embodiment, the initial valve positions are in a blocking or OFF position thereby blocking irrigation fluid flow to the surgical site and blocking suction from the surgical site. The metered valve in Dorsey '796 is generally rectangular in shape with the irrigation source line and suction source line affixed to the valve at a position normal to the delivery line. As stated earlier, the delivery line carries irrigation fluid to the surgical site and, at a different valve setting, provides suction and vacuum from the surgical site.

U.S. Pat. No. 5,391,145 to Dorsey discloses an irrigation control for endoscopic unit. U.S. Pat. No. 5,573,504 to Dorsey discloses a composite irrigation suction probe and valve. U.S. Pat. No. 5,679,111 to Hjertman discloses a device for dosing a liquid preparation. This '111 patent discloses an injection device provided for continuously variable metering and administration of a liquid preparation. The device has a holder for a multi-dose injection cartridge. U.S. Pat. No. 5,674,204 to Chanoch discloses a medication delivery pen cap with an actuated dose delivery clutch. U.S. Pat. No. 5,599,314 to Neill discloses a syringe with an incrementally actuated plunger. U.S. Pat. No. 4,883,472 to Michel discloses an injection device with utilizes an exchangeable pre-filled syringe.

The following patents disclose valving systems that are not utilized in surgical procedures.

U.S. Pat. No. 5,456,448 to Chou (discloses a touch button controlled water stop mounted in a fixed pipe line carrying water, e.g. water to a shower); U.S. Pat. No. 5,421,552 to Wang et al. (discloses a foot operated valve); U.S. Pat. No. 4,956,755 to Maglice et al. (discloses a two position mechanical switch to control a flashlight); U.S. Pat. No. 4,383,477 to Nilsson et al. (discloses a ventilator valve control); U.S. Pat. No. 4,106,508 to Berlin (discloses a clamp used for occlusion of blood vessels); U.S. Pat. No. 4,771,985 to Gross et al. (discloses a hand controlled faucet); U.S. Pat. No. 3,220,695 to Downey et al. (discloses a push button drain valve); U.S. Pat. No. 3,046,802 to Cupedo (discloses a stop valve); U.S. Pat. No. 4,221,236 to Rosenberg (a step valve); U.S. Pat. No. 4,221,238 to Madsen (an intermittent valve); U.S. Pat. No. 5,546,983 to Clare (a shut off valve); and U.S. Pat. No. 5,806,404 to Sher (a rotary piston valve).

There is a need for an in-line hand operated valve that is simple to use and that easily fits within the hand of an operator.

OBJECTS OF THE INVENTION

It is an object of the present invention to provide an in-line, hand operated valve for controlling one, and preferably both, medical irrigation fluid and suction to and from a surgical site.

It is another object of the present invention to provide a cylindrical or a torpedo shaped hand held valve for controlling irrigation fluid and suction to and from a surgical site.

It is another object of the present invention to provide a valve and a valving method whereby the operator control surfaces are on opposing sides, the mechanical valving switch systems in the valve provide audible, tactile and preferably both audible and tactile responses to the operator.

It is another object of the present invention to provide a variable flow control by permitting the operator to depress the operator control surface and hence the valve stem through a throw distance between a click open and a click close position.

It is a further object of the present invention to utilize a click open and click close mechanism similar to that used in connection with ball point pen cartridge controls which, during a click open operation, causes the point of the ink cartridge to protrude beyond the pen body and, during a click close operation, causes the ink pen cartridge tip to retract within the pen body.

It is a further object of the present invention to provide click open and click close operator control surfaces at opposing sides of the cylindrical or torpedo shaped valve body.

It is another object of the present invention to provide the operator control surfaces at a positions substantially maintaining the cylindrical shape or the torpedo shape of the valve body when the valve blocks or closes OFF irrigation flow and suction flow through the valve body.

It is another object of the present invention to provide an irrigation and suction flow control valve which is simple to manufacture, inexpensive and easy to operate.

It is a further object of the present invention to provide an irrigation and suction control valve which is disposable.

SUMMARY OF THE INVENTION

The in-line hand operated valve controls the flow of at least one, and preferably both, medical irrigation fluid and suction respectively to and from a surgical site via a delivery line. In one working embodiment, irrigation fluid is supplied to the valve via a first source line and suction is supplied to the valve via a second source line. The valve body defines, in a working embodiment, source ports in fluid communication with the irrigation source fluid line and the suction source line. At the other end of the valve body, a delivery port is defined and is in fluid communication with the delivery line. The valve body includes at least one, and preferably two, internal fluid carrying channels. The internal channel is in fluid communication with the respective source port and the delivery port. At least a portion of the internal fluid carrying channel is substantially collapsible. The valve includes an operator actuated stem (in a working embodiment two stems, one for each of the irrigation valve switch and the suction valve switch) having a compressor member acting on and closing and opening the collapsible segment of the fluid carrying channel or fluid carrying body. A biasing element (such as a spring or other resilient body) keeps the valve stem and the compressor element in either an open or a closed state. A two position interlocking mechanical switch is coupled to the valve stem. In one position, the compressor element is extended and in a second position, the compressor element is withdrawn to achieve the open and closed state of the fluid carrying channel or body. In a working embodiment, two valve stems are used, each with a compressor member, two independent biasing elements are utilized and two mechanical two position switches are utilized. Further enhancements include operator control surfaces that are on opposing side wall surfaces of the generally cylindrical or torpedo shaped valve body. In a preferred embodiment, the valve is normally closed and the operator control surfaces are substantially co-extensive with the cylindrical or torpedo shaped valve body. To open the valves, the control surfaces are depressed thereby enabling the operator to quickly detect the state of valve position without visual confirmation (a tactile response system). Another enhancement of the present invention includes utilization of audible clicks to notify the operator when the open or closed state is achieved by each mechanical switch system controlling the position of the valve stem and the compressor member. The method of providing a valve control utilizes these shape and click open and click close switch systems.

BRIEF DESCRIPTION OF THE DRAWINGS

Further objects and advantages of the present invention can be found in the detailed description of the preferred embodiments when taken in conjunction with the accompanying drawings in which:

FIG. 1 is a perspective view of the suction and irrigation control valve in accordance with the principles of the present invention;

FIG. 2 diagrammatically illustrates the irrigation and suction valve used in an a surgical suite;

FIG. 3 diagrammatically illustrates a partial, cross-sectional view of the irrigation and suction valve;

FIG. 4 diagrammatically illustrates the schematic view of the internally disposed collapsible tube or fluid carrying body in the valve, the compressor member and stationary wall opposite the compressor member;

FIG. 10 diagrammatically illustrates a perspective view of one type of valve stem, compressive member and a stem portion of the click open click close mechanical switch;

FIG. 11 diagrammatically illustrates the stem which is part of the two position mechanical switch;

FIG. 12 diagrammatically illustrates another mechanical element of the two position mechanical switch; and FIGS. 13A and 13B diagrammatically illustrate the valve stem, compressive member, and another element of the two position mechanical switch and FIG. 13B diagrammatically illustrates a different type of control surface which is mounted on the exterior side of the valve stem shown in FIG. 13A.

DETAILED DESCRIPTION OF THE PREFERRED EMBODIMENTS

Figure 5:
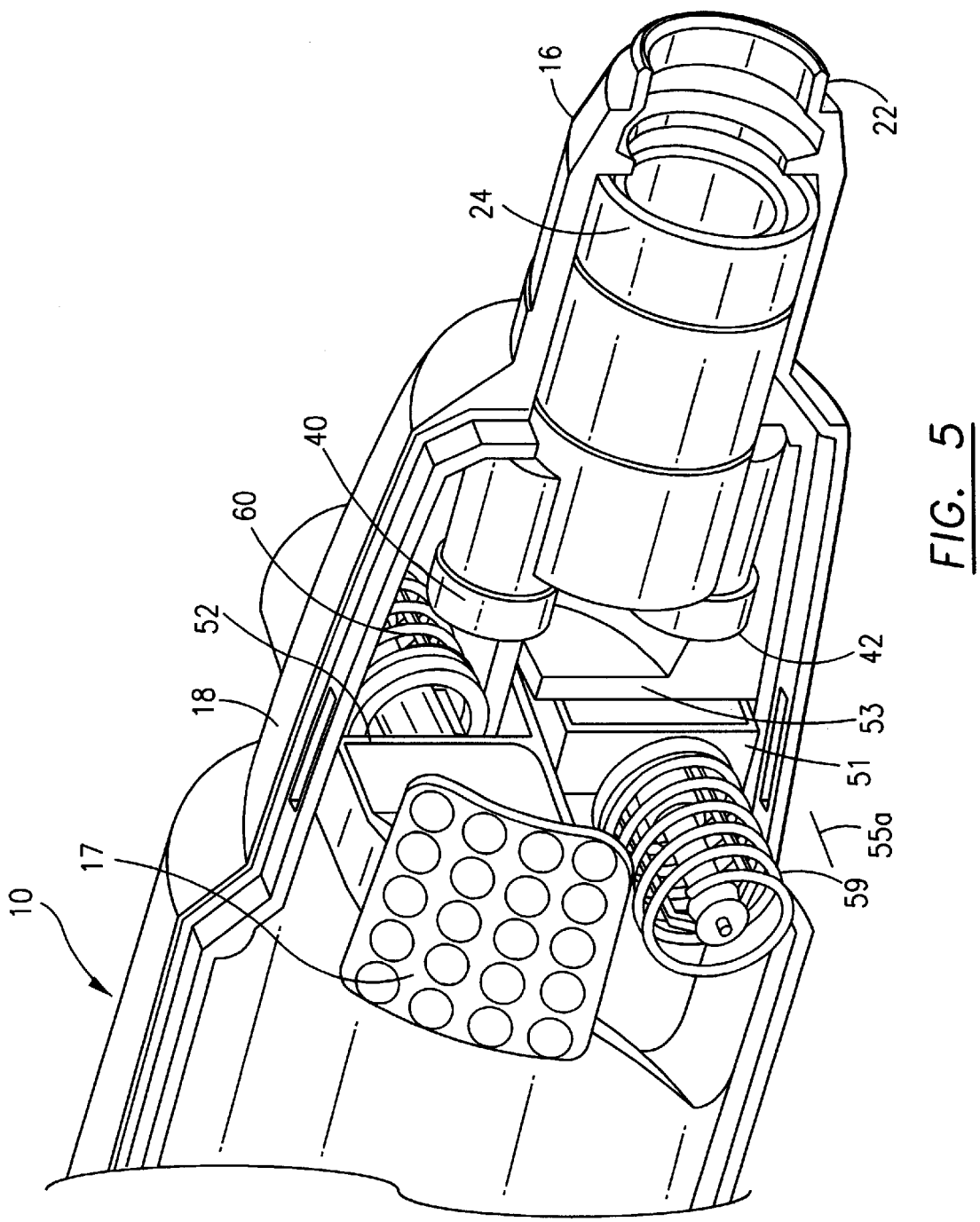
FIG. 5 diagrammatically illustrates a detailed view of the valve control and the click open and click close mechanism in accordance with the principles of the present invention.

The present invention relates to a hand operated irrigation and/or suction valve (and preferably a valve that controls both irrigation fluid and suction) to and from a surgical site and a valving method.

FIG. 1 diagrammatically illustrates in-line, hand operated valve 10 having a generally cylindrically shaped valve body 12. The term "in-line" is used herein as a reference to a valve that controls fluid or suction between a supply and a delivery tube or hose. In a preferred embodiment, valve body 12 is torpedo shaped with a blunt or truncated rear end 14 and a substantially cone shaped fore end 16. Valve body 12 is sized to fit within the hand of an operator. An operator control surface 17 is co-extensive with generally cylindrical section 18 of the generally conical nose portion 16 of valve body 12. In a preferred working embodiment, the co-extensive position of operator control surface 17 provides both a tactile and a visual confirmation to the operator that this portion of valve 10 has closed the fluid channel or collapsible fluid carrying body inside valve 10. This valve system is in an OFF state. In contrast when operator control surface 17 is depressed and is not co-extensive with surface section 18, in a preferred embodiment, the mechanical switch (discussed in detail below) opens the fluid carrying channel or fluid carrying body in valve 10 and permits either irrigation fluid to flow from the source line to the delivery line or delivers suction from the source line to the delivery line which permits evacuation of fluid, debris and sometimes gas from the surgical site (a valve ON state). Variable control is provided by depressing control surface 17 through the throw of the valve switch. The total valve stem throw may exceed the click on, click off stem throw.

FIG. 2 diagrammatically illustrates in-line hand operated valve 10 coupled to source lines 6, 8 which respectively carry irrigation fluid and suction to and from valve 10. Nose section 16 of valve 10 is coupled to delivery line 4 which leads, in the illustrated embodiment, to a handle 3 and a nozzle leading to surgical site 1. Valve 10 is called "an in-line" valve because the valve is hand operated and blocks or controls the flow of either irrigation fluid or suction to and from surgical site 1. It should be appreciated that although the preferred embodiment shows a two valve system, valve 10 can be reconfigured to contain only a single irrigation fluid or suction fluid valving mechanism. However in a working embodiment, valve 10 controls the flow of irrigation fluid from source line 6 to delivery line 4 and ultimately to surgical site 1 as well as controls suction and removal of fluid, debris and gas from surgical site 1 via delivery line 4 to suction source line 8 (i.e., a two valve system).

FIG. 3 diagrammatically illustrates a partial, cross-sectional view of valve 10. Similar numerals designate similar items throughout the drawings. Valve 10, in a working embodiment, includes a generally hollow body 20 defining a generally planar end cap at terminal end 14. At forward end 22, a hose coupler member 24 is adapted to closely fit and fluidly seal the proximal end of delivery tube 4 (FIG. 2). Source tubes 6, 8 (not shown in FIG. 3 but shown in FIG. 2) fluidly seal to rear end tube couplers 26, 28. Tube couplers 26, 28 are maintained in a stationary position by plate 30. Opposite tube coupler ends 26, 28, rigid internal tube couplers 32, 34 are established. In the illustrated embodiment, two internally disposed, substantially collapsible fluid carrying bodies or fluid channels 36, 38 extend between internal tube coupler members 32, 34 and forwardly disposed internal tube couplers 40, 42. In a preferred embodiment, these channels or fluid carrying bodies 36, 38 are made of soft silicone tubing.

In the working embodiment, valve 10 defines two pinch valves or click on-click off mechanical switch mechanisms. One of these click on-click off mechanical switch mechanisms include operator actuated control surface 17. As diagrammatically shown in FIGS. 3 and 4, collapsible fluid carrying tube 38 is pinched between movable valve stem compression member 51 and stationary wall 53. Double headed arrow 55 signifies the extension and withdrawal of compression member 51 and stationary symbol 57 signifies that wall 53 remains stationary with respect to movable compressor member 51. Internal collapsible hose 38 is compressible at least over the segment spanning compressor member 51 and stationary member 53. Internal fluid tube 38 is coupled to fore end internal hose coupler 42 and rear end hose coupler 34. In a working embodiment, the entire tube 38 is soft and compressible.

It should be noted that FIG. 4 shows compressor member 51 being withdrawn to compress or pinch internal tube 38 against stationary element 53. The term "withdrawn" is used in a manner similar to the term "retract" in that both terms reference nearby outer portions of the valve body. However, the mechanical switch and valve can be modified such that the extension of compressor member 51 pinches tube 38 against a stationary support wall. In another words, support wall 53 can be mounted on the opposite side of collapsible tube 38 than the tube side illustrated in FIG. 4. Basically, the valve stem and mechanically coupled compressor member can close the valve by retraction (see FIG. 4) or extension dependent upon the internal construction of the valve 10.

FIG. 5 diagrammatically illustrates a detailed perspective view of the front end of the interior of valve 10. In this view, internal tubes 36, 38 are not illustrated. Compressor member 51 is biased or forced in the direction shown by arrow 55a by spring 59. This is the valve OFF, compressor withdrawn position. With respect to the other mechanical switch and valve, operator control interface 17 is coupled or connected to compressor member 52. Compressor member 52 is biased in the direction opposite arrow 55a by spring 60. Compressor member 51 pinches and closes the internal tube against stationary wall 53. The other stationary wall for member 52 is not shown.

Figure 6:
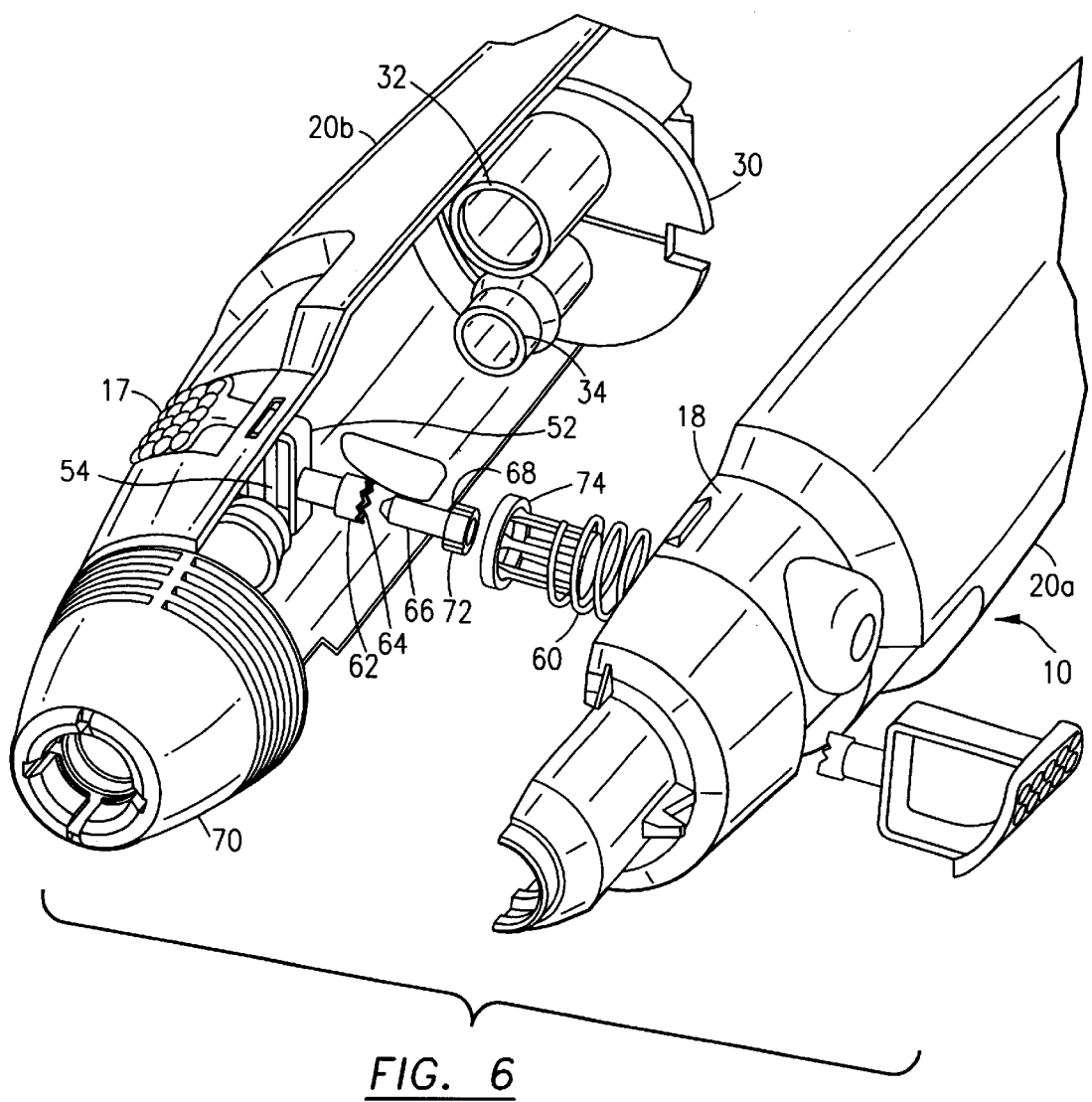
FIG. 6 diagrammatically illustrates an exploded view of the valve body and one of the click open and click close mechanical two position switches used in conjunction with the present invention.

FIG. 6 diagrammatically illustrates a partial, exploded perspective view of valve 10. In a preferred embodiment, valve 10 has two semi-circular, generally cylindrically shaped valve bodies 20a and 20b. Plate 30 provides support for valve bodies 20a, 20b at the rear end of the body. At the front end, nose cone 70 (described later) is part of the generally cylindrical and preferably torpedo shaped valve 10.

User control surface 17 is coupled to compressor member 52. Compressor member 52 squeezes or pinches the internal, highly flexible and collapsible tube 36 (FIG. 3) between it and stationary wall 54. Spring 60 biases or forces compressor element 52 to a position closing the compressor element and pinching tube 36 against stationary wall 54. Other types of biasing systems may be utilized including springs, coils, and solid compressible and resilient elements. Rather than utilizing a spring in compression, a spring in extension pulling compressor bar 52 radially outward away from the axial centerline of valve 10 may be utilized.

Valve 10 includes a two position interlocking mechanical switch or a click on-click off switch. As used herein, the mechanical switch or the click on, click off switch is similar to the extension and retraction control for a ball point pen. This click on-click off two position mechanical switch utilizes a stem 62 having a plurality of sloped control ridges or control surfaces 64. A rotating member 66 has matching and mating sloped control surfaces 68 which mate with control surfaces 64 of stem 62. In addition, rotating member 66 includes radially outward ridges 72 that cooperate with radially in board channels in cage 74. In this manner, when the user or operator first depresses control surface 17, the control surface creates a depression beneath the cylindrical or torpedo shaped valve body 20b. This radially inward mechanical action causes rotating member 66 to rotate by action of control surface 68 riding on control surface 64. Rotation stem 66 turns in accordance with radially inward channels in cage 74 and stem 62 falls within deep groove channels in either cage 74 or stem 66. This causes a large opening between compressive member 52 and stationary wall 54 thereby opening fluid to pass through collapsible hose or tube 36 (a valve ON position). Suction works in a similar manner. Upon the second depression of operator control surface 17, rotating member 66 again rotates in accordance with the radial channels in cage 74, and control surfaces 64, 68 are moved with respect to each other such that compressive member 52 is fully withdrawn from the click on position of the mechanical switch. Further mechanical details of the click on-click off, two position mechanical switch are well documented in other publications. However, the utilization of such a click on, click off switch in an in-line, hand operated irrigation and suction control valve for medical application purposes is new and different.

Figure 7:
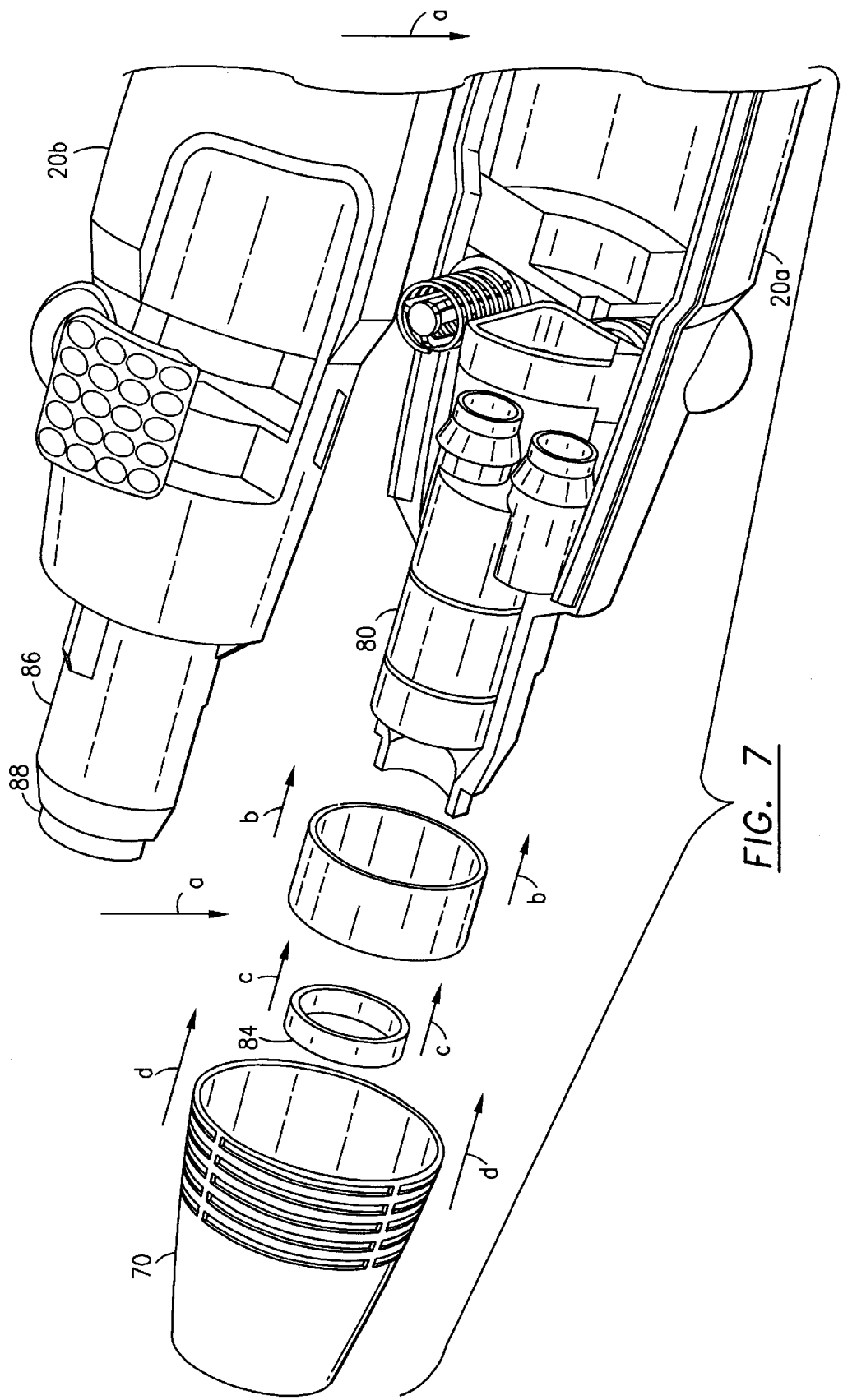
FIG. 7 diagrammatically illustrates an exploded, partial view of the partially assembled valve in accordance with the principles of the present invention.

FIG. 7 diagrammatically shows semi-hemispherical valve body 20b separated from complementary valve body 20a. Confluence chamber 80 is placed in the inside of the fore end of valve bodies 20a, 20b. In order to quickly and securely lock confluence body 80 and valve bodies 20a, 20b together, ring 82 and supplemental ring 84 is placed on proximal nose segment 86 and distal nose segment 88 of the valve bodies. The sequence of assembly of this general portion of valve 10 includes placing confluence chamber 80 in the forward portion of valve body 20a, placing valve body 20b on body 20a per the direction shown by arrow a in FIG. 7, moving large ring 82 in the direction shown by arrow b onto proximal nose section 86 of bodies 20a, 20b and then moving small ring 84 as shown by arrow c onto distal nose section 88. Towards the end of the process, nozzle member 70 is moved in direction d onto the front end of assembled valve bodies 20a, 20b. Rings 82, 84 are preferable metal (e.g. steel).

Figure 8:
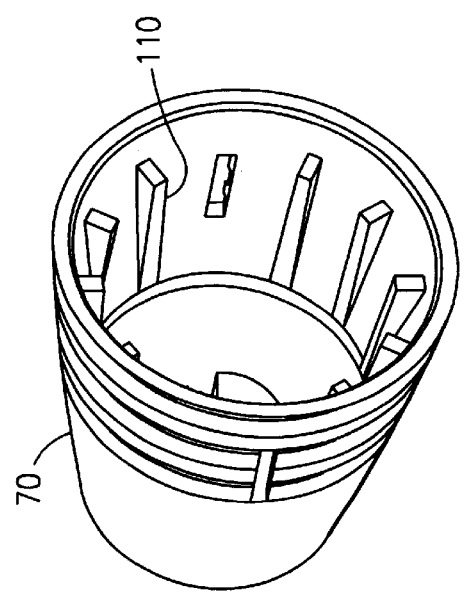
FIG. 8 diagrammatically illustrates a perspective view of the nose cone of the valve.

FIG. 8 diagrammatically shows nozzle 70 having internal support ridges 110. Internal support ridges 110 stabilize nose cone 70 on the valve body.

Figure 9A:
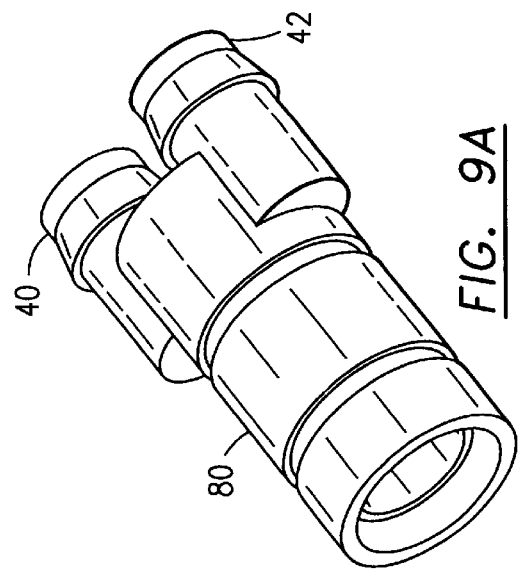
FIGS. 9A and 9B diagrammatically illustrate perspective views of the fluid joint defining the confluence of the two internal fluid tubes and an internal view of that fluid joint.
Figure 9B:
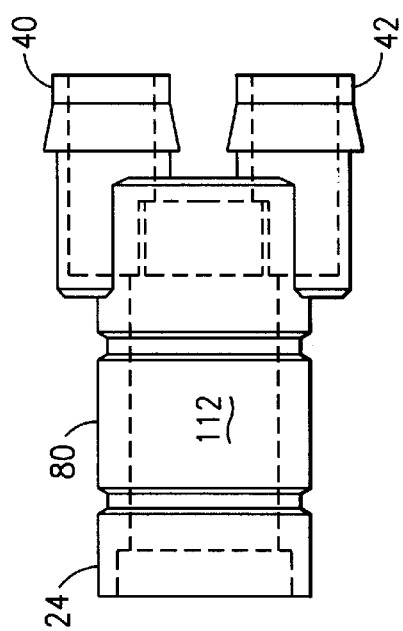

FIGS. 9A and 9B diagrammatically show confluence chamber 80. FIG. 9A shows a perspective view of confluence chamber. FIG. 9B shows in dashed lines the internal chambers of confluence or fluid joint chamber 80. One internal collapsible tube is mounted onto coupling 40 and the other internal collapsible tube is mounted onto coupling 42. As shown in FIG. 5, these are positions near the front end of the valve which is the location for delivery tube 4. See FIG. 2. Hence, delivery tube 4 (FIG. 2) fits within tube coupling 84 opposite the dual tube couplings 40,42. Coupling 84 defines a delivery port for fluid and suction. In FIG. 3, couplers 26, 28 define two source ports for the valve 10. Chamber 112 of fluid joint 80 provides fluid communication between delivery port, essentially defined by tube coupler 24, and the internal fluid carrying tubes attached to internal tube couplers 40, 42.

FIG. 10 diagrammatically illustrates a perspective view of valve stem 130 which includes operator interface 17 and compressor member 52 and part of the click on-click off mechanical switch. This switch part is stem 62. It should be noted that the switch parts may be placed at reversed or opposite locations than those locations shown herein.

FIG. 11 shows a detailed view of rotating member 68, slope control surfaces 68 and radially extensive members 72.

FIG. 12 shows a detailed view of cage 74, radially in board extending guides 120 and positioning stem 122. Positioning stem 122 fits within an aperture 123 and rotating stem 66.

FIGS. 13A and 13B diagrammatically show valve stem 130 wherein operator control 17 (FIG. 13B) is removably mounted via a complementary tab and locking hole system 128, 131. Tab or locking hole 131 is formed as part of valve stem 130 in FIG. 13A. FIG. 13A also shows slope control surfaces 64 and radial depression 124 on the stem for the related two position mechanical switch. The throw of the two position mechanical switch or click on, click off switch is distance th shown in FIG. 13A. This is the distance between the lower part of control slope 64 and the lower part of radial channels 124. The term "lower" used with respect to stem 62 refers to items radially outboard from the axial centerline of the valve 10.

As stated earlier, the present invention can be figured to operate and control irrigation fluid singularly or irrigation fluid and suction (a dual operation valve).

The following table provides some exemplary data for a working embodiment of the invention. For example, it takes about 7 pounds of force to close and turn OFF fluid at 15 psi. This may be decreased to 10 pounds during further development.

Exemplary Dimension and Parameter Table
  overall valve length about 7 in.
  supply line inside diameter (I.D.) about 0.3 in.
  delivery line I.D. about 0.5 in.
  internal tube I.D. about 0.25 in.
  internal tube material: silicone, 30–40 durometer (softness) throw of valving bar about 0.2 in.

The claims appended hereto are meant to cover modifications and changes within the scope and spirit of the present invention.

What is claimed is:

1. An in-line, hand operated valve for controlling the flow of one of medical irrigation fluid and suction respectively to and from a surgical site, said one of irrigation fluid and suction applied to said valve via a source line and said one of irrigation fluid and suction delivered to said surgical site via a delivery line, said valve comprising:
   a body defining a first port in fluid communication with and adapted to be coupled to said source line carrying said one of said irrigation fluid and said suction and a second port in fluid communication with and adapted to be coupled to said delivery line;
   an internally disposed, substantially collapsible fluid carrying body in fluid communication with said first and second ports;
   an operator actuated valve stem having a compressor member acting on and closing and opening said internally disposed fluid carrying body; and
   a biasing element acting on said valve stem and compressor element to keep said fluid carrying body in one of an open and a closed state; and
   a two position, interlocking mechanical switch coupled to said valve stem, said two position switch having a first position extending said compressor element and a second position withdrawing said compressor element.

2. An in-line, hand operated valve as claimed in claim 1 wherein said body is elongated and said operator actuated valve stem has an operator control surface movably disposed normal to said elongated body.

3. An in-line, hand operated valve as claimed in claim 2 wherein said body has a front end adjacent said second port and a rear end adjacent said first port.

4. An in-line, hand operated valve as claimed in claim 2 wherein said body is generally cylindrical in shape and said operator control surface is substantially co-extensive with said cylindrical body when said compressor member closes said internal fluid carrying body.

5. An in-line, hand operated valve as claimed in claim 1 wherein said valve is adapted to be connected with said two source lines, one source line carrying irrigation fluid and the other source line carrying suction, wherein said first port is a first source port and said valve includes a second source port adapted tube said first source port coupled to said irrigation source line and the second source port adapted tube coupled to said suction source line, said collapsible fluid carrying body is a first internal fluid carrying body and said valve including a second internal substantially collapsible fluid carrying body, said first and second fluid carrying bodies respectively coupled to said first and second source ports, said valve stem is a first valve stem, said compressor member is a first compressor member, said biasing element is a first biasing element, said mechanical switch is a first mechanical switch, said valve including a second valve stem, a second compressor member, a second biasing element and a second mechanical switch, said first and second valve stem, compressor member, biasing element and mechanical switch respectively operatively associated with said first and second internal fluid carrying bodies, said valve including a fluid conjoining chamber disposed intermediate said second port, which is operative as a delivery port, and closable segments of said first and second fluid carrying bodies.

6. An in-line, hand operated valve as claimed in claim 5 wherein said body is elongated and said first and second operator actuated valve stems have respective operator control surfaces movably disposed in opposing positions on and normal to said elongated body.

7. An in-line, hand operated valve as claimed in claim 6 wherein said body has a front end adjacent said second port and a rear end adjacent said source ports.

8. An in-line, hand operated valve as claimed in claim 6 wherein said body is generally cylindrical in shape and said operator control surfaces are substantially co-extensive with said cylindrical body when said respective compressor member closes said corresponding internal fluid carrying body.

9. An in-line, hand operated valve as claimed in claim 8 wherein said first and second internal fluid carrying bodies are tubes.

10. An in-line, hand operated valve as claimed in claim 9 wherein each mechanical switch includes a non-rotating post and an interfitting rotating stem, one of said post and said stem having a plurality of generally sawtooth, uniformly sloped control surfaces and the other of said post and stem having alternating deep and shallow sloped control surfaces which interlock with said uniformly sloped control surfaces to position said post at one of an extended position and a confined position with respect to said stem.

11. An in-line, hand operated valve for controlling the flow of one of medical irrigation fluid and suction respectively to and from a surgical site, said one of irrigation fluid and suction applied to said valve via a source line and said one of irrigation fluid and suction delivered to said surgical site via a delivery line, said valve comprising:

a valve body, sized to be grasped by an operator's hand, and defining a source port in fluid communication with and adapted to be coupled to said source line carrying said one of said irrigation fluid and said suction and a delivery port in fluid communication with and adapted to be coupled to said delivery line;

an internal, fluid carrying channel, in fluid communication with said source and delivery ports, said fluid carrying channel having a substantially collapsible segment defined thereby;

an operator actuated valve stem having a compressor member acting on and closing and opening said collapsible segment of said fluid carrying channel; and a biasing element acting on said valve stem and compressor element to keep said fluid carrying channel in one of an open and a closed state; and a two position, interlocking mechanical switch coupled to said valve stem, said two position switch having a first position extending said compressor element and a second position withdrawing said compressor element to achieve said open and closed state of said fluid carrying channel.

12. An in-line, hand operated valve as claimed in claim 11 wherein said body is elongated and said operator actuated valve stem has an operator control surface movably disposed normal to said elongated body.

13. An in-line, hand operated valve as claimed in claim 12 wherein said body is generally cylindrical in shape and said operator control surface is substantially co-extensive with said cylindrical body when said compressor member closes said internal fluid carrying channel.

14. An in-line, hand operated valve as claimed in claim 11 wherein said valve is adapted to be connected with two source lines, said source line being a first source line carrying said irrigation fluid and said valve utilized with a second source line carrying said suction, wherein said source port is a first source port adapted to be coupled to said irrigation source line and the valve includes a second source port adapted to be coupled to said suction source line, said internal fluid carrying channel being a first fluid carrying channel and said valve including a second internal fluid carrying channel, said first and second channels having respective substantially collapsible segments, said valve stem being a first valve stem, said biasing element being a first biasing element, said mechanical switch being a first mechanical switch, said valve including a second valve stem, a second compressor member, a second biasing element and a second mechanical switch, said first and second valve stem, compressor member, biasing element and mechanical switch respectively operatively associated with said first and second internal fluid carrying channels, said valve including a fluid conjoining chamber disposed intermediate said delivery port and said collapsible segments of said first and second fluid carrying channels.

15. An in-line, hand operated valve as claimed in claim 14 wherein said valve body is elongated and said first and second operator actuated valve stems have respective operator control surfaces movably disposed in opposing positions on and normal to said elongated body.

16. An in-line, hand operated valve as claimed in claim 15 wherein said valve body is generally cylindrical in shape and said operator control surfaces are substantially co-extensive with said cylindrical body when said respective compressor member closes said corresponding internal fluid carrying channels.

17. An in-line, hand operated valve as claimed in claim 16 wherein said first and second internal fluid carrying channels are tubes.

* * * * *